United States Patent [19]

L'Esperance, Jr.

[11] Patent Number: 5,207,668
[45] Date of Patent: May 4, 1993

[54] METHOD FOR OPTHALMOLOGICAL SURGERY

[75] Inventor: Francis A. L'Esperance, Jr., Englewood, N.J.

[73] Assignee: VISX Incorporated, Santa Clara, Calif.

[21] Appl. No.: 708,744

[22] Filed: May 31, 1991

Related U.S. Application Data

[63] Continuation of Ser. No. 493,337, Mar. 14, 1990, abandoned, which is a continuation of Ser. No. 891,169, Jul. 31, 1986, abandoned, which is a continuation-in-part of Ser. No. 780,335, Sep. 26, 1985, abandoned, which is a continuation-in-part of Ser. No. 740,276, Jun. 3, 1985, abandoned, which is a continuation-in-part of Ser. No. 552,983, Nov. 17, 1983, abandoned.

[51] Int. Cl.$^5$ ............................................. A61B 5/06
[52] U.S. Cl. ................................... 606/5; 606/10; 606/12
[58] Field of Search ............... 128/898, 395, 397, 398; 606/2-6, 10-19

[56] References Cited

U.S. PATENT DOCUMENTS

| | | | |
|---|---|---|---|
| 4,156,124 | 5/1979 | Macken et al. | 219/121.6 |
| 4,173,980 | 11/1979 | Curtin | 606/180 |
| 4,793,330 | 11/1990 | Azema et al. | 606/5 |

OTHER PUBLICATIONS

"Excimer Laser Surgery of the Cornea", by Trokel et al; Am. J. Ophthalmology; vol. 96, Dec. 1983, pp. 710-715.

"In vivo Experiments with the Excimer Laser Technical Parameters & Healing Processes", by Seiler et al; Ophthalmologica, Basel, vol. 192, pp. 65-70 (1986).

"Carbon Dioxide Laser Beam Control for Corneal Surgery" by Keates et al.; Ophthalmic Surgery; vol. 12, No. 2; Feb. 1981, pp. 117-122.

"Advanced Techniques in Corneal Microsurgery Volume 2 Corneal Surgery" by Gerard; The C. W. Mosley Co., St. Louis 1981.

*Primary Examiner*—David M. Shay
*Attorney, Agent, or Firm*—Hopgood, Calimafde, Kalil, Blaustein & Judlowe

[57] ABSTRACT

The invention contemplates controlled ablation of the cornea, using ultraviolet laser radiation, wherein irradiated flux density and exposure time are so controlled as to achieve desired depth of the ablation. Sculpturing action results from precharacterized distribution of flux density across the cross-section of laser-beam projection, in the context of beam size, at cornea incidence, to match the area to be ablated, and the duration of exposure determines the extent of curvature change. Illustrative techniques and situations are disclosed, for myopia correction, for hyperopia correction, and for astigmatism correction.

6 Claims, 3 Drawing Sheets

FIG. 9.
FIG. 12.
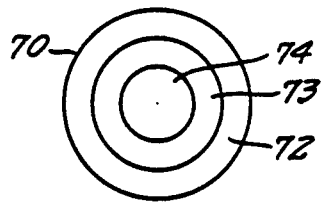
FIG. 10.
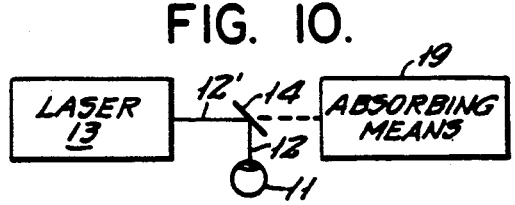
FIG. 13.
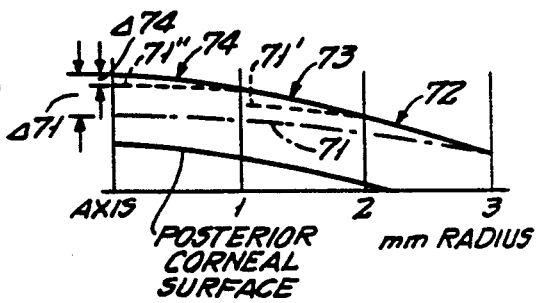
FIG. 11.
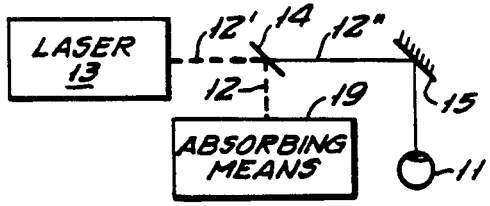
FIG. 14.
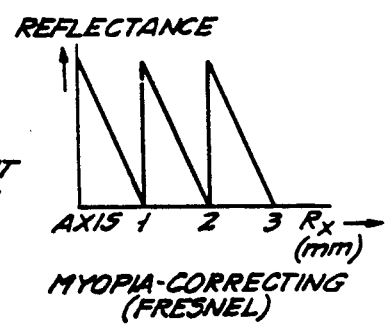
MYOPIA-CORRECTING (FRESNEL)
FIG. 16.
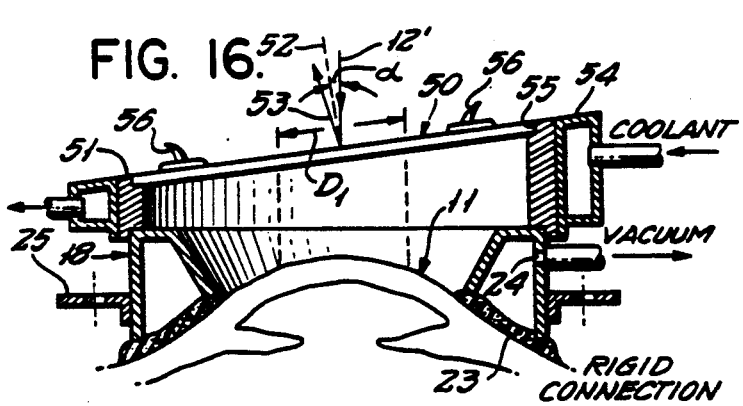
FIG. 17.
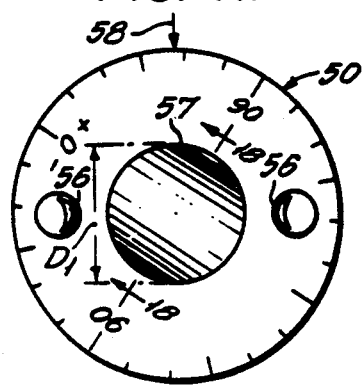
FIG. 18.
REFLECTANCE ALONG AXIS 18-18
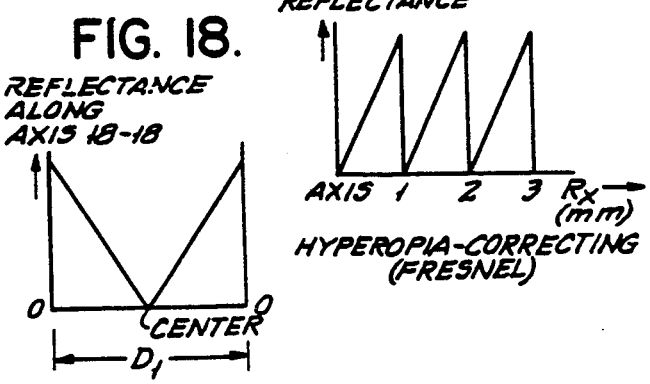
FIG. 15.
HYPEROPIA-CORRECTING (FRESNEL)

METHOD FOR OPTHALMOLOGICAL SURGERY

This application is a continuation of copending application Ser. No. 07/493,337, filed Mar. 14, 1990, and said application Ser. No. 07/493,337 is a continuation of abandoned application Ser. No. 891,169, filed Jul. 31, 1986; said abandoned application Ser. No. 891,169 is a continuation-in-part of abandoned application Ser. No. 780,335, filed Sep. 26, 1985; said abandoned application Ser. No. 780,335 is a continuation-in-part of abandoned application Ser. No. 740,276, filed Jun. 3, 1985; and said abandoned application Ser. No. 740,276 is a continuation-in-part of abandoned original application Ser. No. 552,983, filed Nov. 17, 1983.

BACKGROUND OF THE INVENTION

The invention relates to that aspect of ophthalmological surgery which is concerned with operations upon the external surface of the cornea.

Operations of the character indicated include corneal transplants and keratotomies; such operations have traditionally required skilled manipulation of a cutting instrument. But, however keen the cutting edge, the mere entry of the edge into the surface of the cornea necessarily means a wedgelike lateral pressure against body cells displaced by the entry, on both sides of the entry. Such lateral pressure is damaging to several layers of cells on both sides of the entry, to the extent impairing the ability of the wound to heal, and resulting in the formation of scar tissue.

My said original application Ser. No. 552,983 includes a background discussion of the effects of various available wavelengths of laser radiation in ophthalmological surgery and, in particular, surgery performed on the anterior surface of the cornea. It is explained that radiation at ultraviolet wavelengths is desirable by reason of its high photon energy. This energy is greatly effective on impact with tissue, in that molecules of tissue are decomposed on photon impact, resulting in tissue ablation by photodecomposition. Molecules at the irradiated surface are broken into smaller volatile fragments without heating the remaining substrate; the mechanism of the ablation is photochemical, i.e., the direct breaking of intramolecular bonds. Photothermal and/or photocoagulation effects are neither characteristic of nor observable in ablations at ultraviolet wavelengths, and cell damage adjacent the photodecomposed ablation is insignificant. The order of magnitude of this ablative process, in the case of radiation exposure at ultraviolet wavelengths (in the range of about 400 nm or less), is that an energy density of 1 joule/cm$^2$ incises to a depth of micron (1$\mu$). Said original patent application discloses a technique of scanning a laser beam over the anterior surface of a cornea in such a controlled pattern as to sculpture said surface, imparting a new curvature to said surface, whereby to achieve optical correction of an optically deficient eye. But the scanner and scanner control to perform the technique are relatively complex and expensive.

In my application Ser. No. 742,225, filed Jun. 6, 1985, I describe a non-scanning technique of changing optical properties of the eye by ultraviolet laser radiation wherein controlled changes in laser-spot size perform ablative sculpturing of the cornea, resulting in a suitably corrected profile. The described technique involves programmed use of zoom-lens and/or various characterized masking techniques.

BRIEF STATEMENT OF THE INVENTION

It is an object of the invention to provide an improved apparatus and technique for surgically operating upon the outer surface of the cornea.

Another object of the invention is to simplify and reduce the cost of apparatus and technique for surgically modifying optical properties of the eye through surgical procedure on the outer surface of the cornea.

It is a specific object to achieve the above objects with surgical techniques and apparatus for reducing a myopic, for reducing a hyperopic, and/or for reducing an astigmatic condition of an eye.

Another specific object is to provide an improved surgical technique in performing corneal-transplant operations.

A still further specific object is to achieve the above objects with automatic means for safely applying ultraviolet irradiation in surgical procedures on the cornea.

It is also an object to achieve the above objects without use of scanning techniques or apparatus.

The invention achieves these objects with apparatus which effectively fixes the position of an eye with respect to a non-scanning laser characterized by ultraviolet radiation, at an energy level capable of achieving controlled ablative photodecomposition of the cornea, namely, of the epithelium, Bowman's membrane, and stroma levels of the cornea. Irradiated flux density and exposure time are so controlled as to achieve desired depth of the ablation.

As distinguished from the scanning and variable-spot procedures of said original and copending applications, a sculpturing action results from interposing an optical screen, wedge, or mirror of pre-characterized transmittance or reflectance in the path of laser-beam projection to the eye. More particularly, the cross-section of laser-beam projection to the eye is such as to accord with the full frontal area of desired curvature correction, e.g., 6 or 7-mm diameter, centered on the optical axis of the eye; and the interposed device is characterized as to transmittance or reflectance which varies as a function of radius about the optical axis. In this circumstance, laser radiation at cornea impingement is of correspondingly characterized flux density, with correspondingly characterized ablative penetration capability, per unit exposure time. Thus, for myopia or hyperopia correction, the number of diopters of achieved curvature correction will be a function of exposure time, for cross-sectionally characterized radiation which is circumferentially uniform at any given radius; and for astigmatism correction, the number of diopters of achieved cylindrical correction, at a given prescribed angular orientation across the optical axis, will also be a function of time, but for cross-sectionally characterized radiation which is of symmetrically reducing flux density on opposite sides of the selected orientation axis.

DETAILED DESCRIPTION

The invention will be illustratively described in detail, in conjunction with the accompanying drawings, in which:

FIGS. 8 and 9 are diagrams corresponding to FIGS. 5 and 6, respectively, to illustrate ablative corneal sculpture performed with apparatus as in FIG. 1, for the case of correcting a hyperopia condition;

FIGS. 10 and 11 are schematic diagrams, respectively illustrating two different use configurations of the invention;

FIGS. 12, 13, 14 and 15 are simplified diagrams to illustrate use of the invention to achieve Fresnel-type optically corrective contours at the anterior surface of the cornea, FIG. 14 graphically depicting myopia-correction, and FIG. 15 graphically depicting hyperopia-correction;

FIG. 16 is a view similar to FIG. 2 to illustrate a further embodiment;

FIG. 17 is a plan view of one of a plurality of optically selectable beam-splitting elements usable in the embodiment of FIG. 16, the selected element being used in connection with laser-ablated correction for an astigmatic condition;

FIG. 18 is a diagram graphically depicting reflectance as a function of diametral distance at the section 18—18 of FIG. 17.

Figure 1:
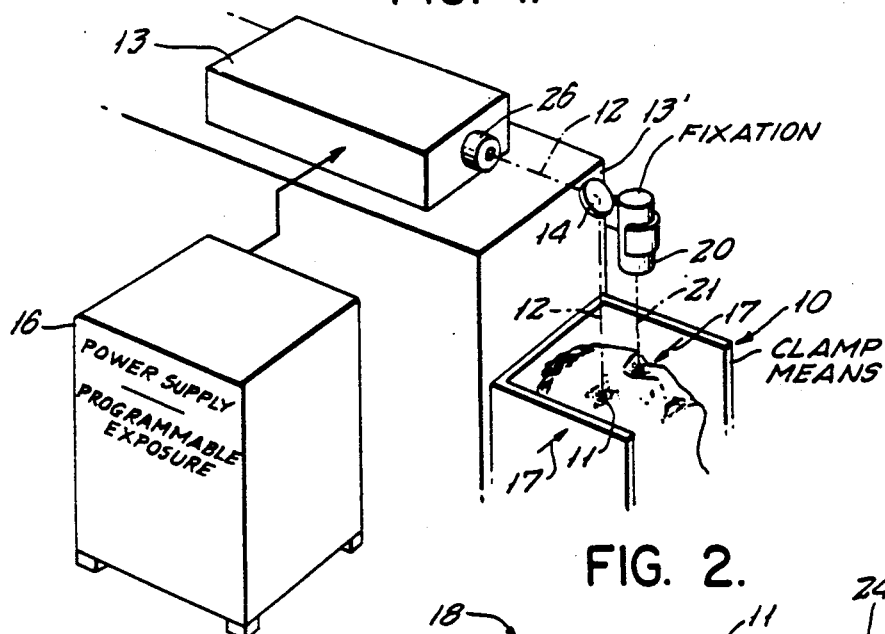
FIG. 1 is a schematic diagram in perspective, to show the general arrangement of operative components of the invention.

In FIG. 1, clamp means 10 is shown for fixed retention of the head of a Patient (reclined, face up) such that the eye 11 to be operated upon is fixedly aligned with a downwardly folded portion 12 of the central axis 12' of beam output from a stationary laser device 13, supported by a table or other base 13'. The optical system of laser-beam projection to eye 11 includes (a) means 26 establishing the cross-section of the laser beam as a circle of 3 or 3.5-mm radius, corresponding to the corneal frontal area to be subjected to laser action, and (b) a reflector 14 of precharacterized reflectance, whereby the laser radiation incident upon the cornea is a circumferentially uniform function of radius about the central axis of the projected beam 12. A cabinet 16 is shown by legend to include a power supply for the laser, and cabinet 16 is also shown to include programmable means, which may include a microprocessor, for exposure control.

Clamp means 10 preferably includes means, symbolized at 17, to stabilize the patient's head via opposed engagements at the region of his temples, and an eye-retaining fixture (18, FIG. 2) peripherally engages eye 11 at the corneal-scleral area. Also preferably, an optical-fixation device 20 is adjustably fixed, as to the table or base 13'. Illustratively, device 20 includes a sighting reticle and lens, whereby the eye 11' not being operated upon can view the reticle as if at infinity; the sighting alignment 21 for device 20 is parallel to the axis 12, and it will be understood that adjustable means (not shown) may provide an adjustable offset, as needed for accommodation of the patient's interpupillary distance and to adapt to the particular mounted offset of device 20 from axis 12. For an operation on the other eye 11', the eye 11 will be available for similar fixation, in conjunction with another fixation device (not shown) and associated adjustably offsetting means; alternatively, the fixation device 30 may be adjustably mounted at correct offset on the opposite side of beam 12. For purposes of operating on eye 11', clamp means 10 will have been indexed laterally with respect to laser 13 to the extent aligning axis 12 with the eye (11') then to be operated upon, thereby positioning eye 11 for use of the fixation device.

Figure 2:
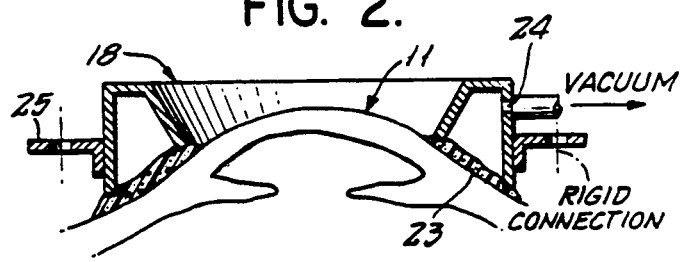
FIG. 2 is a simplified view in longitudinal section, showing an eye-retaining fixture used with the apparatus of FIG. 1.

The eye-retaining fixture 18 of FIG. 2 is seen to comprise a hollow annulus, having a convergent axial-end wall 23 of air-permeable material contoured to engage and retain the eye via a scleral-corneal region. A side-port connection 24 to a vacuum pump enables retention of eye engagement to wall 23, and outward lug or flange means 25 enables rigid aligned and spaced connection of fixture 18 to laser 13 and its beam 12 via means suggested by legend in FIG. 2, such means being omitted from FIG. 1 for reasons of more simplified showing.

The laser selected for use at 13 preferably emits in the ultraviolet, namely, at wavelengths of less than substantially 400 nanometers. Such emissions for gas lasers are characteristically at 351-nm for xenon-fluoride lasers, 337-nm for nitrogen lasers, 308-nm for xenon-chloride lasers, 248-nm for krypton-fluoride lasers, 193-nm for argon fluoride lasers, and 157-nm for fluorine lasers; and within this range, frequency-doubling techniques applied to other lasers, including crystal lasers, provide further alternative sources.

One of the existing commercial excimer-laser products of Lambda Physik GmbH, Göttingen, Germany, for example their Model EMG 103 operating with argon-fluoride, is satisfactory for use as laser 13; for this product, maximum energy per pulse is 200 millijoules, with a pulse-repetition rate of 200 per second, $3 \times 10^5$ shots (pulses) being available from a single charge of the involved gas, before reducing to 50 percent of specified power at this repetition rate, it being noted that full rated power is not necessarily required in use of the present invention. Pulse width is about 15 nanoseconds, and typical beam dimensions are rectangular; as shown, however, the opening in a mask 26 reduces the laser beam to a circular section.

Figure 3:
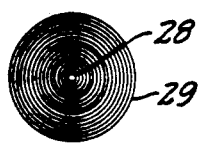
FIGS. 3, 4, 5, 6 and 7 are simplified diagrams to illustrate the nature of ablative corneal sculpture, performed with apparatus as in FIG. 1, for the case of correcting a myopia condition.
Figure 8:
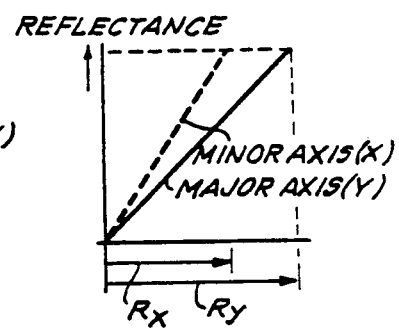

For the situation depicted in FIG. 1, the reflecting surface of element 14 is inclined at 45 degrees to the axis of laser-beam incidence, whereby, Pursuant to the precharacterized nature of element 14 the laser beam is reflected on axis 12, at 90 degrees from axis 12', with axis 12 aligned with the optical axis of eye 11. The maximum area of element 14 usable for reflecting beam 12' is thus an ellipse wherein the minor axis equals the diameter of the laser beam and the major axis is $\sqrt{2}$ times the minor axis; FIG. 3 is a simplified diagram in aid of describing the circumferentially uniform radial distribution of laser-flux density directed to eye 11, by reason of reflection at 14, in the circumstance of precharacterized reflectance to be described in connection with FIG. 5. Shading techniques are inadequate to demonstrate the precharacterized reflectance, and therefore the nature and action of such precharacterization will be described generally, first, as an optical step wedge to produce a stepped ablation profile (FIG. 7) and, then, as a smoothly progressive wedge graphically defined by FIG. 5 or FIG. 8.

Figure 4:
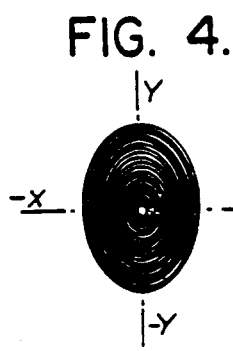
Figure 6:
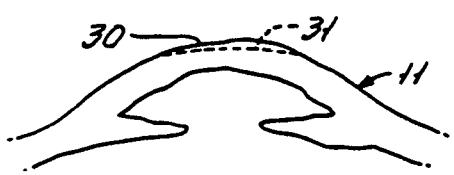
Figure 7:
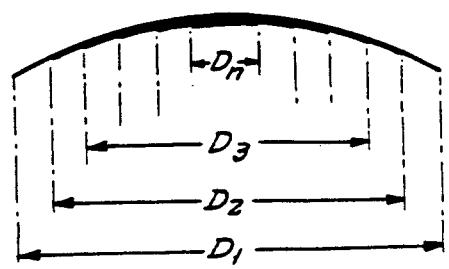

FIGS. 6 and 7 are illustrative of use of the invention in an optically corrective ablation of the anterior surface 30 of eye 11, wherein a myopia problem is to be solved, meaning that the curvature of surface 30 is of too-short radius to establish focus at the retina, for the case of distant objects. On the other hand, the dashed line 31 represents the ultimate curvature to which the anterior surface of the cornea should be modified to achieve a diopter-reducing corrective effect. To achieve the curve 31, the minimum desired photodecomposition is at the outer boundary 29, and the maximum is at the center 28. To produce this result, maximum laser-beam flux density characterizes ablative action at the center of the exposed area of the cornea, and minimum (zero, or substantially zero) laser-beam flux density is presented at the circumference of the exposed area. Between these radial extremes, flux density is graduated, being suggested in FIG. 3 as a succession of concentric annular bands which, for myopia reduction, will be understood to be the product of a similar succession of bands of circumferentially uniform reflectance, wherein reflectance increases as a function of decreasing radius. But since the reflector 14 must be elliptical, each of the successive bands of progressively increasing reflectance must be elliptical, as suggested by the plural ellipses of FIG. 4, having like major/minor axis ratios, wherein reflectance along the minor axis will be understood to be stepped from maximum at the center, to minimum at the extremes ($-X$, $+X$), and similarly wherein reflectance along the major axis will be understood to be stepped from maximum at the center to minimum at the extremes ($-Y$, $+Y$).

FIG. 7 is a very much simplified diagram to represent the progressive ablative effect of a given time exposure of eye 11 to ultraviolet-laser radiation which is characterized by the described distribution of flux densities, attributable to a corresponding distribution of reflectance at 14. At the outer annulus where reflectance is least, the flux density is least and therefore little or no ablative penetration of the cornea occurs for this outer band (between diameters $D_1$, $D_2$, in FIG. 7). In the next inward annular band (between diameters $D_2$, $D_3$), an increment of reflectance accounts for an incremental advance in ablative penetration; and further such incremental advances in ablative penetration will occur in cumulative relation, as a function of decreasing radius of successive bands. The final band is a small central circle of diameter $D_n$ where maximum shading thickness indicates maximum ablative penetration, due to maximum reflectance at the elliptical center of reflector 14.

The stepped progressively thicker shading of FIG. 7 (meaning correspondingly stepped increasing ablative penetration of the cornea) will be seen to define a new, larger-radius curvature for the ablated region of the cornea. Theoretically, there is a stepped character to the new profile, but for a sufficiently great number of annuli of progressively varying flux density, individual steps cease to appear discrete, and a sufficiently smooth new spherical anterior surface characterizes the cornea. This is particularly so after a post-operative period of about two days, by which time a thin epithelial layer will have spread into smooth and protective coverage of the newly characterized surface.

Figure 5:
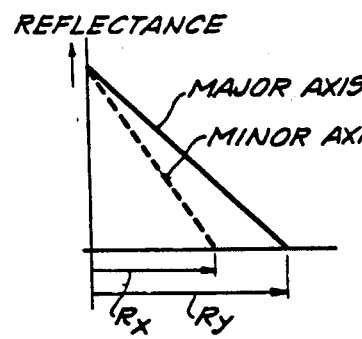

As indicated generally above, the stepped nature of precharacterized reflectance at 14 may be replaced by a mirror surface of continuously varying reflectance, the same being graphically suggested by FIG. 5, wherein precharacterized reflectance of mirror 14 is described as being at maximum at the center, and at minimum (zero) at the periphery, whether observed along the major axis or along the minor axis, directions being shown for minor-axis increasing radial extent ($R_x$) and for major-axis increasing radial extent ($R_y$). Naturally, the ablated newly formed curvature obtained with a smoothly varying reflectance, as described for FIG. 5, will necessarily be correspondingly smooth and free of any stepped effects.

It will be seen that the amount of myopia-reducing correction achieved via precharacterized reflectance at 14 will be a function of exposure time. Thus, with a sufficient data base of diopter reduction for exposure time at given maximum flux density, it will become possible to set with precision the time required for a given diopter reduction for a given patient. For a great preponderance of cornea-curvature abnormalities, the same reflector 14 can serve to produce different degrees of curvature reduction, representing say, for relatively short exposure times, the one or two diopters of reduction needed by some Patients, or, with longer exposure times, the two or more diopters of reduction needed by other patients. Also, since it may be desirable to operate upon certain patients with the caution of one increment at a time, a desired reduction of say three diopters can be achieved by a two-diopter reduction in a first visit, followed by a period of several days to permit the patient to judge and accommodate to the change, before deciding whether and to what more precise extent to make the next corrective but shorter ablative exposure, using the same apparatus and mirror 14.

What has been said for myopia reduction applies equally for hyperopia correction, wherein reflectance at 14 must be such as to project greatest flux density of the laser beam at the outer diameter $D_1$ of the exposed area of the cornea, with flux density decreasing proggressively to zero at the central area. This may be a stepped progression, as suggested by the multiple concentric circles of FIG. 3 (and ellipses of FIG. 4) or a continuous progression, as suggested by the curves of FIG. 8. In either event, the resulting ablated profile will be an increase in cornea curvature (i.e., shorter radius of curvature) over the exposed area, as indicated for the change in FIG. 9 from the hyperopic curvature 60 to the corrected curvature 61 (dashed line).

Described components of FIG. 1 will be recognized by reference numbers in FIG. 10, wherein the reflector 14 is shown as a beam splitter, as in the case wherein the characterized reflecting surface is applied to a suitable transparent flat substrate, as of quartz, in which case there is a transmitted beam 12" as well as the reflected beam 12 issuing from the beam splitter. As shown, the transmitted beam 12" is collected and dissipated by suitable means 19 which is generally designated as an absorber, but such designation will be understood to apply for the situation in which means 19 is also a means of measuring or metering dosage, in that what is transmitted will always bear a fixed proportional relation to the dosage administered via reflection along axis 12 to the eye.

Similarly, and as shown in FIG. 11, the transmitted beam on axis 12" may be the beam used, via reflection at 15, for ablation of the cornea of eye 11, while the reflected component on axis 12 is directed to the absorbing means 19. In this event, myopia-reduction is achieved when beam splitter 14 is characterized by maximum reflectance at the maximum elliptical perimeter and by minimum (substantially zero) reflectance at the center, intervening perimeters being of progressively reducing reflectance with decreasing offset from the center. And hyperopia-reduction is achieved when reflectance is greatest at the center and minimal (substantially zero) at the maximum elliptical perimeter.

The foregoing discussion in connection with FIGS. 1 to 5 presupposes a pulsed laser, exemplified by an excimer laser. But other lasers are known to emit at presently suitable energy levels and at ultraviolet wavelengths of present utility, and these other lasers will emit continuously for periods of controlled duration. For example, an organic-dye laser utilizing the proper organic dye can be made to produce laser emission in the region of 380-nm when pumped by ultraviolet laser sources such as a continuous-wave frequency-quadrupled neodymium-YAG laser operating at 266-nm; in this case, the organic-dye laser emission at 380-nm can be frequency doubled by a proper non-linear crystal such as a potassium-deuterium-phosphate (KDP) crystal or a potassium-titanium-phosphate (KTP) crystal to an emission wavelength at 190-nm. The showing of FIGS. 1 to 9 will thus be understood to illustrate the further case wherein ultraviolet laser radiation on axis 12 is of continuous-wave nature, for a treatment duration predetermined by programming at 16, the timing being preset by the surgeon based on his experience, or being set as determined from a data base of accumulated experience, for diopter change as a function of exposure time.

The arrangement of FIGS. 12, 13, and 14 illustrates that above-discussed principles of the invention are further applicable to corrective sculpture of the cornea to achieve a Fresnel-type distribution of the desired ultimate curvature, which can be either hyperopia-correcting or, as shown, myopia-correcting. Such an operation (i e., Fresnel-type) would be used when, in the surgeon's considered judgment, a single smoothly developed corrected curvature would entail excessive removal of tissue at the involved region of necessarily deepest cut. To avoid too deep a cut, FIGS. 12 and 13 illustrate that an ultimately reduced-curvature surface, as at 31 in FIG. 6 (dashed line 71 in FIG. 13), is achieved in annular increments within the field bounded at 70. In the outer one of these annuli (72), the curvature and depth of cut are precisely as would have applied to generate the continuous curve 71 (i.e., without Fresnel steps). But the intermediate annular area 73 effectively achieves a continuation of curve 71 with much less volume of corneal excision. Finally, the inner circular area 74 effectively completes curve 71, with minimal removal of corneal tissue.

The removal of tissue at the center is denoted Δ 74 for the Fresnel cut 74 of FIGS. 12 and 13 and, comparatively, is but a small fraction of the maximum removal depth Δ 71 which would have been needed to achieve the same optical correction with the smoothly developed corrected single-curvature surface 71. FIG. 14 graphically and generally depicts the precharacterized distribution of reflectance for the minor axis of the elliptical reflector, using the arrangement of FIG. 1 or FIG. 10 to achieve myopia-reducing Fresnel-type ablations of the nature described for different annuli 72, 73, 74. Within each of these annuli, greatest reflectance is at the inner dimension ($R_x$), and reflectance progressively decreases to minimum at the outer dimension ($R_x$). Thus, for a given exposure, the new curvature 71 can be achieved within outer annulus 72, with axially offset continuation of this new curvature at 71' in annulus 73; and, at further axial offset, there is further effective continuation of the new curvature at 71", within the central circular area 74.

FIG. 15 generally depicts reflectance considerations at reflector/beam-splitter 14, for use of the FIG. 1 or FIG. 10 arrangements to achieve a hyperopia reduction. As shown, in each of the concentric annuli of a Fresnel-type ablative cut for this purpose, reflectance is minimal (substantially zero) at the inner dimension ($R_x$) and Progressively increases to maximum at the outer dimension ($R_x$).

What has been said for the curves of FIGS. 14 and 15 in the context of a FIG. 1 or FIG. 10 use of the invention is the exact reverse of what applies for use of the transmitted beam 12", as in FIG. 11. Specifically, high inner-dimension reflectance, diminishing to lowest reflectance at the outer dimension of each Fresnel-type annulus (as depicted in FIG. 14) translates into greatest flux-density transmission at 12" at the outer dimension ($R_x$), diminishing to lowest (substantially zero) flux density at the inner dimension ($R_x$) of each Fresnel-type annulus; this distribution pattern accounts for hyperopia reduction for a given exposure via axis 12". Similarly, the reflectance characteristic depicted in FIG. 15 accounts for myopia-reduction for cornea exposures via axis 12".

FIG. 16 illustrates an embodiment of the invention which utilizes the full circular-section beam of laser output on axis 12' (which may have been folded downward by a fully reflective surface, not shown), at incidence with an inclined beam-splitter 50 which is removably mounted to an adapter 51 carried by the eye-retaining fixture 18, described in connection with FIG. 2. However, in FIG. 16, the inclination angle α of normal 52 (to the surface of splitter 50) from axis 12 is purposefully small so that the characterized reflectance for the reflected component 53 may, for practical purposes, be of circular rather than elliptical nature. FIG. 3 may thus be taken with FIG. 8 in illustration of circumferentially uniform distribution of reflectance at 50 over the beam diameter $D_1$, where for a myopia-reducing exposure one selects a splitter 50 characterized by greatest flux density of transmitted laser radiation in the central region of the beam, decreasing to least (substantially zero) flux density at the maximum diameter $D_1$. And FIG. 3 may similarly be taken in conjunction with FIG. 5, in illustration of reflectance at 50 over the beam diameter $D_1$, where for a hyperopia-reducing exposure one selects a splitter 50 characterized by greatest flux density of transmitted laser radiation at the maximum diameter $D_1$, decreasing to least (substantially zero) flux density at the central region of the beam.

It will be understood that in a FIG. 16 use of the invention, the angle α should be selected such that the reflected component on axis 53 is diverted from interference with other hardware, except for interception by suitably positioned absorbing means (not shown) of the nature indicated at 19 in FIGS. 10 and 11.

FIG. 16 also shows Provision of an annular manifold 54 having inlet and outlet Ports for accommodation of coolant flow, should heat dissipation be necessary in view of the mounting of adapter 51 in proximity to the eye 11. And to aid in on/off manipulation of selected differently characterized circular beam-splitter discs 50, with respect to nested position in the seating counterbore 55 of adapter 51, each such disc may be equipped with a pair of opposed lug fittings 56 for finger engagement outside the area (diameter $D_1$) of precharacterized reflectance, which also is to be understood as precharacterized transmittance, where the transmittance function is inversely related to the reflectance function.

FIGS. 17 and 18 illustrate that the embodiment of FIG. 16 has further utility when the characterized circular beam-splitting area (diameter $D_1$) of a selectively available circular disc 50' is characterized to effect an astigmatism-reducing ablative correction via the transmitted component of beam-splitting; the characterization must be such as to pass maximum flux density on a diameter alignment across the characterized area, with progressive reduction of flux density as a function of lateral offset from the said diameter, such reductions being symmetrical on opposite sides of the said diameter alignment. In FIG. 17, shading for reflectance in the characterized region 57 of disc 50' is therefore heaviest at outermost lateral offsets from the single-diameter alignment identified with a zero-degree index marking at the edge of the disc. Other angle gradations are shown for the range to 90 degrees positive and to 90 degrees negative, being in the opposite directions away from the zero-index mark. These angles are to be read against a fixed reference mark 58 which will be understood to be inscribed in adapter 51, and it will be additionally understood that suitable keying means (not shown) or other means of angular referencing to the vertical or horizontal meridian of the eye are either provided in the assembly of adapter 51 to fixture 18 or are independently set by the surgeon so that the zero index position of disc 50' has true relation to the relevant meridian orientation. This being the case, angular indexing manipulation of disc 50' to a prescription astigmatism axis orientation with respect to reference 58 is all that is necessary for correct orientation for ablative surgery. All that then remains is to set the exposure-timing program, for ablative diopter reduction to the desired or prescribed extent.

While the invention has been described in detail for various embodiments, it will be understood that modifications may be made without departing from the scope of the invention. For example, the showings of distributed transmittance or reflectance as a linear function of radius (or effective radius) are intended as illustrative of a smooth continuum of the progression, which may be a non-linear function for certain corrective purposes.

Figure 19:
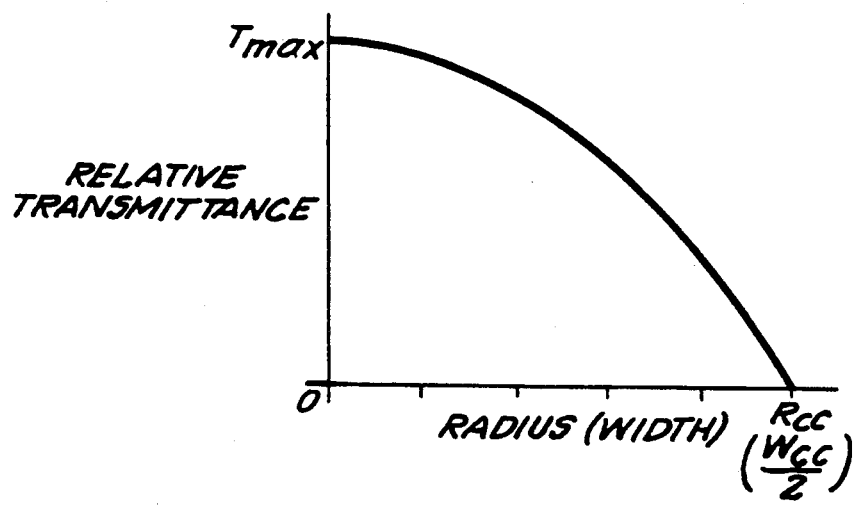
FIGS. 19 and 20 are similar diagrams graphically illustrating different special-purpose refinements of the invention.
Figure 20:
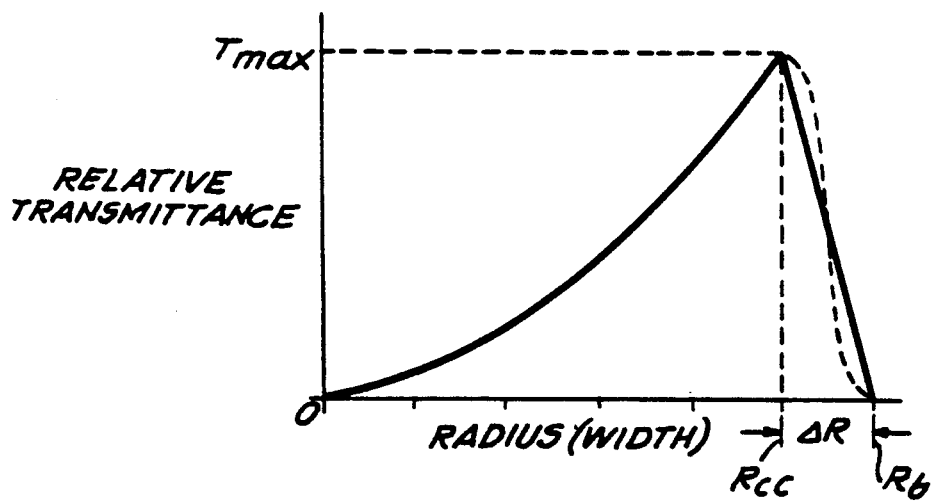

More particularly, the curves of FIGS. 19 and 20 illustrate that such non-linear functions are quasi-parabolic whether the exposure is myopia-correcting (FIG. 19) or hyperopia-correcting (FIG. 20). In the case of FIG. 19, maximum transmittance is at the central axis of the projected laser beam 12, so that for any diameter across a right section of said beam, the transmittance function (i.e., flux density distribution profile) is quasi-parabolic, peaking for maximum laser-beam flux density, on the central axis and reducing to zero at the maximum radius $R_{cc}$ of the circular area in which myopia-curvature correction is to be achieved.

In the hyperopia-correcting case of FIG. 20, minimum (i.e., zero, or near-zero) transmittance is at the center of the projected laser beam 12, so that for any diameter across a right section of said beam, the transmittance function (i.e., flux-density distribution profile) is quasi-parabolic, peaking, for maximum laser-beam flux density, at the radially outer limit $R_{cc}$ of the circular area in which hyperopia-curvature correction is to be achieved.

It will be recalled from the hyperopia-correcting discussion in connection with FIG. 9 that deepest penetration of the stroma is at the perimeter of the area of surgery, thus leaving a relatively sharp circular edge, of depth proportional to the quantum of exposure to the laser surgery, i.e., proportional to the magnitude of diopter correction achieved. Such a sharp edge produces a problem for epithelial regrowth over the area of surgery, in that epithelial regrowth is optimum for essentially continuous surfaces, uninterrupted by sharp edges or by sharp discontinuities. To avoid such a sharp-edge development, FIG. 20 additionally shows that the projected laser beam 12 should be of sectional area larger than that over which hyperopia-curvature correction is to be achieved, thus providing for an outer profile-smoothing annulus contiguous to and surrounding the circle of curvature-correction. In FIG. 20, the incremental radius $\Delta R$ defines this annulus; and reduction in transmittance, from maximum at $R_{cc}$ to minimum at the radius $R_b$ of the projected laser beam, is shown to be linear, in the radially outward direction, and between inner and outer limits of the annulus $\Delta R$. Generally, the radial extent $\Delta R$ of the annulus should be in the range of 5 to 15 percent of the radius $R_{cc}$ of the circle of curvature correction, and preferably about 10 percent.

It will be understood that the indicated linear reduction in transmittance will account for minimum slope at all points within the annulus, meaning that for deepest surgical penetration of the cornea (e.g., 100 microns, for a 10-diopter correction over a 5-mm diameter circle of curvature correction), a linear characteristic is best; but for lesser penetrations such as for diopter corrections of up to 5 diopters, a non-linear relationship (as suggested by the dashed-line curve spanning $\Delta R$ in FIG. 20) enables provision (within the radial span $\Delta R$) of continuously smooth curvature transition, from the radius $R_{cc}$ of maximum penetration and radially outward to the untreated adjacent original profile of the cornea.

What has been said above as to minimizing and eliminating sharp-edge development for a hyperopia-correcting sculpture of the cornea also applies for the case of astigmatism-correcting sculpture when the astigmatism is hyperopia-analogous, i.e., when astigmatism-correction requires an increase in the cylindrical radius of curvature in order to reduce or eliminate the astigmatism. In such case, maximum depth of corrective sculpturing penetration of the cornea is at the laterally outer limits of the astigmatism-correcting procedure, leaving relatively sharp edges at these outer limits. These edges are avoided or materially reduced in severity if the laser beam is so precharacterized, laterally outward of these maximum-depth limits, as to reduce in approach to substantially zero flux density. If the curve of FIG. 20 is taken to show relative transmittance (flux-density distribution) laterally outward of the predetermined orientation of astigmatism to be corrected (rather than in terms of radial distribution), then the profile of FIG. 20 is seen as a half section of the transmittance distribution normal to the predetermined direction of astigmatism correction. In similar fashion, FIG. 19 illustrates such distribution for the case of astigmatism that is myopia-analogous, and parenthetical ("width") legends in both FIGS. 19 and 20 can be taken as a showing of the respective astigmatism-correcting profiles.

In the foregoing discussion, fairly consistent reference has been made to reflectors 14 and 50 as beam splitters, i.e., with capability both to transmit and to reflect characterized distributions of transmittance and reflectance properties. The expression "beam splitter" as used herein is to be understood as being only illustrative of filter means to particularly characterize the sectional distribution of flux density in the beam 12 which is projected to the patient's eye. Thus, a suitably characterized circular filter 15 (FIG. 1) in the path of beam projection via a plane mirror at 14 may achieve cornea sculpting of the nature described. Such a filter may be a thin-film gradient filter, or a filter wherein photolith half-tone gradation provides the radially characterized transmittance or reflection properties, or it may be a microporous plate wherein the cluster density of micron-size holes through the plate determines the transmittance characteristic. Available substrates for one or more of such filtering devices may be selected from the group which includes fused silica, lithium fluoride, calcium fluoride, and barium fluoride.

What is claimed is:

1. The method of effecting without mechanical contact an optically correcting change within a predetermined optically used central circular anterior surface area of the cornea of an eye, from an initial curvature requiring mypio correction to a subsequent curvature having improved optical properties, which method comprises predetermining the number of diopeters of needed optically correcting curvature change, using ultraviolet laser radiation in a program of selective ablation of the optically used portion of the anterior surface of the cornea by photodecomposition, with penetration into stroma tissue and volumetric sculpturing removal of corneal tissue to such penetration depth and profile as to characterize the anterior surface with said subsequent curvature, said sculpturing removal being via laser radiation which is characterized by a circular spot having a single density-distribution profile wherein flux density decreases radially outward at least to the perimeter of said predetermined area, determining from said predetermined number of diopters a predetermined maximum ablation depth into the stroma, adjusting laser-beam projection to a limited intensity level at which resultant corneal-tissue ablation per unit time is to an ascertained elemental depth which is but a fraction of said predetermined maximum ablation depth into the stroma, determining from said elemental depth per unit time and from said predetermined maximum ablation depth the amount of exposure time needed to accomplish said predetermined maximum ablation depth and thus said predetermined number of diopters of curvature change, and proceeding with said program for said exposure time predetermined to achieve the predetermined number of diopters of myopia-correcting change.

2. The method of claim 1, wherein the single density-distribution profile is quasi-parabolic.

3. The method of effecting without mechanical contact an optically correcting change within a predetermined optically used central circular anterior-surface area of the cornea of an eye, from an initial curvature requiring hyperopia correction to a subsequent curvature having improved optical properties, which method comprises predetermining the number of diopeters of needed optically correcting change, using ultraviolet laser radiation in a program of selective ablation of the optically used portion of the anterior surface of the cornea by photodecomposition, with penetration into stroma tissue and volumetric sculpturing removal of corneal tissue to such penetration depth and profile as to characterize the anterior surface with said subsequent curvature, said sculpturing removal being via laser radiation which is characterized by a circular spot having a single density-distribution profile wherein flux density increases radially outward at least to the perimeter of said predetermined area, determining from said predetermined number of diopters a predetermined maximum ablation depth into the stroma, adjusting laser-beam projection to a limited intensity level at which resultant corneal-tissue ablation per unit time is to an ascertained elemental depth which is but a fraction of said predetermined maximum ablation depth into the stroma, determining from said elemental depth per unit time and from said predetermined maximum ablation depth the amount of exposure time needed to accomplish said predetermined maximum ablation depth and thus said predetermined number of diopters of curvature change, and proceeding with said program for said exposure time predetermined to achieve the predetermined number of diopters of hyperopia-correcting change.

4. The method of claim 3, in which the single density-distribution profile is quasi-parabolic.

5. The method of effecting without mechanical contact an optically correcting change within a predetermined optically used central circular anterior-surface area of the cornea of an eye, from an initial curvature requiring astigmatism correction to a subsequent curvature having improved optical properties, which method comprises predetermining the number of diopeters and the angular orientation of needed optically correcting change, using ultraviolet radiation in a program of selective ablation of the optically used portion of the anterior surface of the cornea by photodecomposition, with penetration into stroma tissue and volumetric sculpturing removal of corneal tissue to such penetration depth and profile as to characterize the anterior surface with said subsèquent curvature, said sculpturing removal being via laser radiation which is characterized by a circular spot having a single density-distribution profile wherein flux density decreases with symmetry on opposite lateral sides of a diametral alignment across said circular spot, determining from said predetermined number of diopters and angular orientation a predetermined maximum ablation depth into the stroma, adjusting laser-beam projection to a limited intensity level at which resultant corneal-tissue ablation per unit time is to an ascertained elemental depth which is but a fraction of said predetermined maximum ablation depth into the stroma, determining from said elemental depth per unit time and from said maximum ablation depth the amount of exposure time needed to accomplish said predetermined maximum ablation depth and thus said predetermined number of diopters of curvature change, orienting said single density-distribution profile consistent with the predetermined angular orientation of needed optically correcting change, and proceeding with said program for said exposure time predetermined to achieve the predetermined number of diopters and angular orientation of astigmatism-correcting change.

6. The method of claim 5, in which the symmetrical flux-density decrease is quasi-parabolic on opposite lateral sides of said diametral alignment.

* * * * *